United States Patent
Squirrell et al.

(10) Patent No.: US 7,252,975 B2
(45) Date of Patent: Aug. 7, 2007

(54) ANALYTICAL METHOD AND KIT

(75) Inventors: David James Squirrell, Salisbury (GB); Martin Alan Lee, Salisbury (GB)

(73) Assignee: The Secretary of State for Defence, Salisbury, Wiltshire (GB)

( * ) Notice: Subject to any disclaimer, the term of this patent is extended or adjusted under 35 U.S.C. 154(b) by 251 days.

(21) Appl. No.: 10/477,083

(22) PCT Filed: May 7, 2002

(86) PCT No.: PCT/GB02/02096

§ 371 (c)(1),
(2), (4) Date: Apr. 30, 2004

(87) PCT Pub. No.: WO02/090586

PCT Pub. Date: Nov. 14, 2002

(65) Prior Publication Data

US 2004/0175709 A1    Sep. 9, 2004

(30) Foreign Application Priority Data

May 9, 2001    (GB) ................... 0111275.4

(51) Int. Cl.
*C12P 19/34*    (2006.01)
*C12Q 1/68*    (2006.01)

(52) U.S. Cl. .......................................... 435/91.2; 435/6

(58) Field of Classification Search .................. None
See application file for complete search history.

(56) References Cited

U.S. PATENT DOCUMENTS

| 4,735,897 A | 4/1988 | Vary et al. |
| 5,853,990 A | 12/1998 | Winger et al. |
| 6,159,693 A | 12/2000 | Shultz et al. |

FOREIGN PATENT DOCUMENTS

| EP | 0 212 067 A1 | 3/1987 |
| EP | 0639647 A2 | 2/1995 |
| WO | WO 98/04738 | 2/1998 |
| WO | WO 99/46409 | 9/1999 |
| WO | WO 9946409 A1 * | 9/1999 |
| WO | WO 00/22165 | 4/2000 |
| WO | WO 00/49179 | 8/2000 |

OTHER PUBLICATIONS

Eisaki et al., "Pyruvate phosphate dikinase from a thermophilic actinomyces *Microbispora rosea* subsp. aerata: purification, characterization and molecular cloning of the gene," Biochimica et Biophysica, 1999, vol. 1431, pp. 363-373.*

(Continued)

*Primary Examiner*—Young J. Kim
(74) *Attorney, Agent, or Firm*—Kilpatrick Stockton LLP

(57) ABSTRACT

Analytical methods using RNA probes for the detection or analysis of nucleic acid sequences is described. These probes are contacted with a sample suspected of containing the nucleic acid sequence and if they form duplexes, they are hydrolysed. This may be done, for example during an amplification reaction. AMP generated as a result of the hydrolysis is converted to ATP. The ATP may then be detected using bioluminescent reagents.

12 Claims, 1 Drawing Sheet

OTHER PUBLICATIONS

Figure 1:
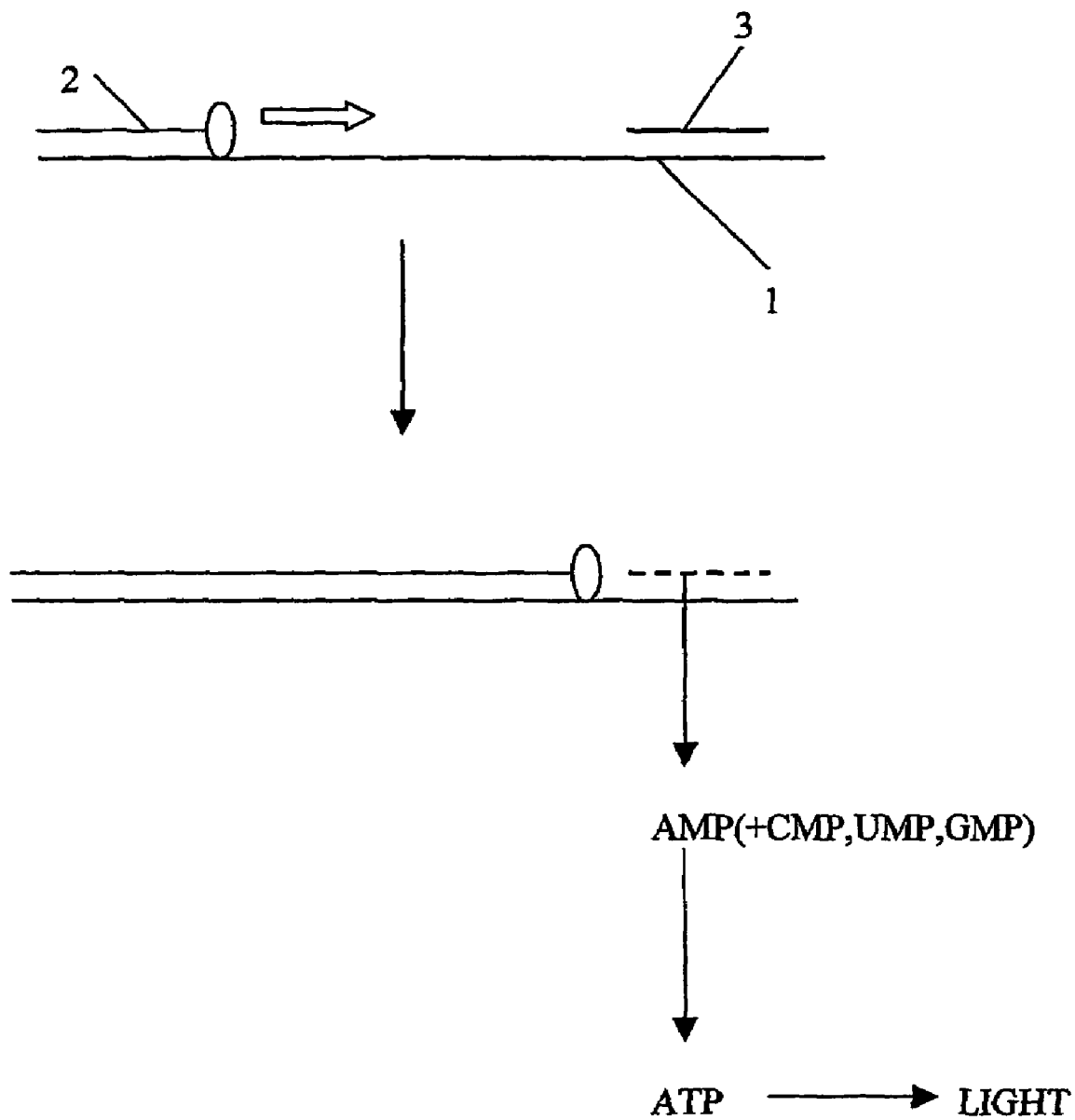

RNase H, catalog # M0297S, [online], [retrieved on Jul. 14, 2006] Retrieved from the New England BioLabs®, Inc. website using internet <URL:http://www.neb.com/nebecomm/products/productM0297.asp>.*

Holland, et al., "Detection of specific polymerase chain reaction product by utilizing the 5'-3' exonuclease activity of thermos aquaticus DNA polymerase," Proceeding of the National Academy of Sciences, vol. 88, pp. 7276-7280, Aug. 1991.

Moyer, et al., "Ultra sensitive assay of RNA application to 100-500 cells," Analytical Biochemistry, vol. 131, No. 1, pp. 190-193, 1983.

Search Report issued in priority Application No. GB0111275.4.

* cited by examiner

ANALYTICAL METHOD AND KIT

CROSS-REFERENCE TO RELATED APPLICATIONS

This application is the U.S. national phase of International Application No. PCT/GB02/02096 filed on May 7, 2002 and published in English as International Publication No. WO 02/090586 A2 on Nov. 14, 2002, which application claims priority to Great Britain Application No. 0111275.4 filed on May 9, 2001, the contents of which are incorporated by reference herein.

The present invention relates to a method of analysing a nucleic acid sequence, for example to detect the presence of a particular sequence within a sample, or to determine the precise sequence of a particular nucleic acid, and to kits and reagents for use in these methods.

Currently there is a wide range of methods of conducting analysis of nucleic acids. Analytical methods may be directed to those that detect the presence or amount of a particular nucleic sequence in a sample suspected of containing that sequence. Other methods elucidate the structure of a nucleic acid to determine its sequence of nucleotides for information or diagnostic purposes.

Amplification reactions are commonly used to effect or assist in this analysis, particularly where the particular nucleic acid sequence is present in only minute amounts. The use of amplification reactions such as the polymerase chain reaction (PCR) for detection of target nucleic acid sequences is well known. One or more primers which are specific for the particular sequence are included in an amplification reaction mixture. These will hybridise to the specific target sequence when in single stranded form within a sample tube. If the target sequence is present, the primer will bind to it, whereupon polymerase enzyme present in the mixture will, at certain temperature conditions, extend the primer to form a complete complementary strand. This material then forms further templates, for amplification in subsequent cycles of denaturation, primer annealing and extension.

The amplified product may be detected, for example on an electrophoretic gel. However, fluorescent labelling methods are now frequently used to detect when an amplification reaction has been effected, and/or to monitor its progress. Examples of such assays include the TAQMAN™ assay, as well as assays described and claimed for example in WO 99/28500, WO 99/28501, WO 99/42611 and WO 99/66071. An assay using labelled ribo-oligonucleotide probes is described in WO 98/04738. Labelling of probes however is a complex process which increases the cost.

Methods for sequencing nucleic acid sequences are also well known. Gel methods are conventional. More recent methods are carried out using devices such as the Pyrosequencer available from Pyrosequencing AB, rely on the generation of a visible signal when a correct nucleotide is added during the construction of a complementary strand on a single stranded nucleic acid template. Other methods for interrogating the identity of a specific base in a nucleic acid sample using pyrophosphorolysis reactions are described in WO 99/46409.

The applicants have found that RNA probes, which are unlabelled, can provide an advantageous means for monitoring or detecting such events.

According to the present invention there is provided a method for detecting or analysing a nucleic acid sequence in a sample, said method comprising contacting said sequence with an RNA probe under conditions such that the probe will bind to the sequence, subjecting any nucleic acid/probe complex to conditions under which RNA probe bound to nucleic acid is hydrolysed to generate adenosine monophosphate (AMP), detecting AMP produced, and relating this to the presence or nature of the nucleic acid sequence in the sample.

RNA probes may be readily hydrolysed by a variety of enzymes, when in double stranded form. These include polymerase enzymes commonly used in PCR reactions such as Taq polymerase. Alternatively they may be hydrolysed by RNAse enzymes, which will hydrolyse them only when in double stranded form, for example as an RNA/DNA duplex. Such duplexes may be formed in the course of an amplification reaction such as a PCR reaction, but this is not necessarily the case.

Hydrolysis of RNA as carried out in the method of the invention produces adenosine monophosphate (AMP). This may be phosphorylated to adenosine triphosphate (ATP) enzymatically either directly or by way of the production of adenosine diphosphate.

ATP may be readily detected using bioluminescent systems, a particular example of which is the luciferase/luciferin detection system. Examples of the application of such detection systems are described for example in WO 96/02665.

Bioluminescent systems such as the luciferase/luciferin system do not react with the deoxyATP (dATP) which is usually added to PCR reactions in order to obtain the polymerase activity required. Thus, they will be able to distinguish between ATP produced as a result of hydrolysis of the RNA probe and any dATP which may be required to be added to the reaction mixture for other purposes.

Bioluminescent detection systems are more sensitive than fluorescent systems. Consequently, the use of RNA hydrolysis probes in analytical methods facilitates the detection of interactions at the nucleic acid level within a sample and so gives rise to enhanced methods of analysis.

In a particular embodiment, the invention provides a method for detecting the presence or amount of a target nucleic acid within a sample, said method comprising denaturing nucleic acids within a sample, contacting these with an RNA hydrolysis probe which is specific for at least a portion of said target nucleic acid so that the probe forms duplexes with the target nucleic acid; adding an enzyme which hydrolyses RNA when in double stranded form (for example as an RNA/DNA duplex) and one or more enzymes or reagents necessary to convert adenosine monophosphate produced to adenosine triphosphate; adding to the sample bioluminescent reagents which react to the presence of ATP, detecting a signal from said bioluminescent reagents and relating that to the presence or amount of the target nucleic acid sequence.

This method will frequently be carried out in the context of an amplification reaction. Thus in a further particular embodiment, the invention provides a method for detecting the presence or amount of a target nucleic acid within a sample, said method comprising conducting an amplification reaction, such as a polymerase chain reaction, in the presence of (a) an RNA probe which is specific for at least a portion of said target nucleic acid; (b) an enzyme which hydrolyses RNA when in double stranded form (for example as an RNA/DNA duplex) and (c) one or more enzymes or reagents necessary to convert adenosine monophosphate produced to adenosine triphosphate; adding to the sample bioluminescent reagents which react to the presence of ATP, detecting a signal from said bioluminescent reagents and relating that to the presence or amount of the target nucleic acid sequence.

Suitably the enzyme which hydrolyses RNA when in double stranded form ((b) above), is the polymerase used in the amplification reaction. Examples of suitable DNA polymerases which may be used in the context of the invention are thermostable polymerases such as *Thermus aquaticus* polymerase (Taq), *Thermus thermophilus polymerase* (Tth), *Thermus species NH* polymerase (TspNH), *Thermus brockianus* polymerase (Tbr) (all obtainable for example from GeneSys Limited, Farnborough, U.K.), *Pyrococcus furiosus* polymerase (Pfu) (obtainable from Stratagene), 9° N7 exo-DNA polymerase, and *Thermococcus litoralis* DNA polymerase (obtainable from New England Biolabs as VENT™ DNA polymerase).

If however, this does not hydrolyse the RNA quickly enough, for example if rapid PCR is being employed, then a suitable RNAse and in particular a DNA dependent RNAse, as would be known in the art, might also be added.

The one or more enzymes necessary to convert adenosine monophosphate produced to adenosine triphosphate ((c) above), may for example be selected from phosphoenolpyruvate synthase which produces ATP directly from AMP in the presence of phosphate and phosphoenolpyruvate, which are also added as a reagent to the reaction mixture. Alternatively, a combination of a nucleoside triphosphate-adenylate kinase and NTP will yield adenosine diphosphate (ADP), which may then be converted to ATP by inclusion or addition of an enzyme such as adenylate kinase.

Yet further examples of suitable enzymes include pyruvate phosphate dikinase such as that described by Eisaki et al, Biochim. et Biophys Acta 1431 (1999) 363-373.

Particularly suitable bioluminescent reagents, which react to the presence of ATP, include luciferin and luciferase, accompanied if necessary by a source of magnesium ions such as magnesium acetate. In the presence of ATP, these reagents produce a luminescent signal, which can be readily monitored for example using conventional luminometer devices.

In generating a signal, these reagents regenerate an AMP molecule, which in the presence of the enzymes and/or reagents of (c), will be reconverted back to ATP. Thus the signal builds up exponentially and so will be readily and rapidly detected. An example of such a system is described by Sakakibara et al., Analytical Biochemistry, 268, 94-101 (1999). This exponential rise in signal may mean that detection can be carried out directly, in circumstances where amplification reactions may previously have been required.

Suitably the bioluminescent reagents are present or added throughout the amplification reaction so that the progress of the reaction can be monitored. Generally speaking, the thermostability of reagents such as luciferase is not sufficient to allow it to be present throughout an amplification reaction and thus, it is suitably added at the end of each cycle. Such information may be used then in the quantification of the target nucleic acid sequence in the sample, using algorithms etc. which are known in the art.

The amplification reaction may be conducted in the usual way, for example by cycling the reaction mixture through denaturation, annealing and extension temperatures.

The reaction as described above could be carried out in a variety of conventional equipment. These include for example a Pyrosequencer (available from Pyrosequencing AB, Sweden), which is already provided with appropriate signal detection means. Alternatively, the reaction may be carried out using block heating devices as described for example in EP-A-0810030 and supplied by The Perkin-Elmer Corporation, rapid hot air thermal cyclers such as the RapidCycler™ and LightCycler™ from Idaho Technologys Inc. or other types of thermal cycler such as those described in WO98/24548.

This method is illustrated diagrammatically hereinafter in FIG. 1. In the initial stage of a PCR reaction, a sample which contains or is suspected of containing a particular nucleic acid sequence is heated to a temperature at which the DNA denatures to form single stranded template strands (1). A conventional PCR primer (2) binds to one end of the template strand, whilst the complementary RNA probe (3) binds elsewhere on the target sequence. The polymerase enzyme then operates during the extension phase of the reaction to extend the primer (2) in the direction of the arrow to form a full-length complementary strand. During the course of this process, the RNA probe (3) will be hydrolysed as illustrated by the dashed line, releasing AMP, which is converted in situ to ATP. This ATP is then detected as a light signal.

The method of the invention may also be adapted for sequencing applications and/or for detecting polymorphisms or variations in DNA or RNA sequences.

In a further aspect, the invention provides a method for determining the sequence of a nucleic acid, said method comprising
(i) binding an RNA probe to a known region of said sequence such that at least one nucleotide at an end of said probe reaches into an unknown or uncertain region of the sequence;
(ii) hydrolysing the RNA probe using an enzyme which hydrolyses RNA when in double stranded form (for example as an RNA/DNA duplex);
(iii) converting adenosine monophosphate produced to adenosine triphosphate;
(iv) adding to the sample bioluminescent reagents which react to the presence of ATP;
(v) detecting a signal from said bioluminescent reagents; and
(vi) relating that signal to the presence of a region of the sequence which is complementary or otherwise to the end of the probe.

In such cases, if the one or more nucleotides at the end of the probe are precisely complementary to the unknown or uncertain sequence, the probe will bind most efficiently to it, whereupon the enzyme will efficiently hydrolyse the bound probe during step (ii). As a result, AMP is generated, which is converted to ATP as described above, and detected using a bioluminescent system.

However, if the nucleotide(s) at an end of the RNA probe is not a correct match for the template DNA, then the effect of the enzyme in (ii) will be to largely dislodge the probe intact, from the template. As a result no significant hydrolysis occurs and this will be reflected in the lack or substantial reduction in any bioluminescent signal generated.

This reaction may be carried out more than once, using probes with different nucleotides at the end regions. For example, if the nucleotide found within the sequence at this position is not known, four different probes, each with a different nucleotide C, G, U and A at the end may be prepared. By conducting the method of the invention with each of these individually, it should be readily apparent which is the correct nucleotide at this position, by the level of the signal generated. A good signal would be expected only in the reaction in which the probe includes the complementary nucleotide at the end.

If desired, more that one unknown nucleotide may be included at the end, for example up to three nucleotides In such cases, probes representing all possible combinations of sequences at the positions may be carried out. It would be expected that the probe which had a precisely complementary sequence at the end would be efficiently hydrolysed.

The end used may be the 3' or the 5' end of the probe, depending upon the nature of the known versus the unknown or uncertain sequence. The enzyme used in step (ii) will be selected with this in mind. Hydrolysis of a tightly bound RNA probe may be better effected when the end is the 3' end and the enzyme used in step (ii) is capable of 3'-5' hydrolysis (as compared to 3'-5' hydrolysis), as often found in enzymes which are regarded as having good "proof-reading" function.

Where a plurality of reactions are carried out, these may suitably be carried out simultaneously in separate reaction tubes, wells or vessels, which are arranged in an array. The tubes, wells or vessels may be cycled together and the signals from each tube monitored using an appropriate positioned luminometer.

Alternatively, a probe may be immobilised on a support, for example of the "dipstick" design, to provide a diagnostic test, for example for a polymorphism or allelic variation in a particular test sequence as outlined below.

The enzymes and reagents used in the method will be similar to those used in the method for detecting the presence or amount of a nucleic acid sample as described above. Similarly the reaction may be carried out in equipment as described above.

The reaction may be used in conjunction with an amplification reaction such as a PCR reaction. For example the reaction may be carried out subsequent to a PCR reaction. At least some stages of the PCR reaction may be effected in order to achieve the hydrolysis in step (ii). However, generally speaking this may not be necessary, since the system itself provides a good amplified signal, as a result of the "recycling" of the AMP detected.

Such methods would be useful in sequencing, where at least a portion of the starting sequence is known (for example a universal priming sequence). Entire sequences can then be resolved, by reiterating the process along the length of the sequence. Parallel reactions to elucidate the sequence may be possible using RNA oligonucleotide libraries as the probes, where for example the sequence is known to contain several conserved regions along its length, for example as occurs during ribotyping. These regions may each be used as the known sequence for locating the RNA probes.

Sequencing the reverse direction by way of confirmation may also be carried out using the method of the invention. Where possible as a result of the presence of conserved regions, this may be done in parallel using an array of reactions.

Alternatively, the methods may be used in the detection of polymorphisms or allelic variations for use in diagnostics. In such cases, the sequence may be broadly known except for a small region of one or more nucleotides which may be uncertain at the locus of the polymorphism or variation. In such cases, the RNA probe is designed such at least an end region nucleotide corresponds to the polymorphism or variation in the sequence, whereupon efficient hydrolysis or otherwise, will indicate whether or not the actual sequence is complementary to the probe sequence or not.

These reactions may be conducted in reaction tubes, wells or vessels as described above. Again, they will conveniently be in an array where multiple reactions are effected.

In yet a further aspect, the invention provides a kit for use in a method as described above. Such kits will comprise at least one RNA probe which is specific for the target sequence and optionally also means for converting AMP to ATP. In the case of the method of detecting polymorphisms, the kit may comprise up to four similar RNA probes, which differ only by the presence of a different nucleotide at the 3' end.

Kits will suitably comprise one or more further reagents for use in the method. In particular, they may also contain bioluminescent reagents such as luciferase and/or luciferin. Other particular optional components of the kit may include primers for use in a particular amplication. In addition, kits may contain a DNA polymerase which hydrolyses RNA or an RNAse as described above.

Other reagents such as buffers, nucleotides, polymerase enzymes etc., which might be required in order to effect an amplification may also be included.

RNA hydrolysis probes therefore provide a very versatile means for generating signals indicating the presence of very specific nucleic acid sequences within a sample. The sensitivity of assays using such probes combined with bioluminescent detection systems is high and signals can be generated rapidly.

The invention claimed is:

1. A method for detecting the presence or amount of a target DNA sequence within a sample, said method comprising conducting a DNA amplification reaction, which uses at least one primer, in the presence of (a) an RNA probe which is specific for at least a portion of said target DNA sequence downstream of the primer; (b) an enzyme which hydrolyses RNA when in the form of an RNA/DNA duplex and (c) one or more enzymes and/or reagents necessary to convert adenosine monophosphate produced to adenosine triphosphate (ATP); adding to the sample bioluminescent reagents which react to the presence of ATP, detecting a signal from said bioluminescent reagents and relating that to the presence or amount of the target DNA sequence.

2. The method of claim 1 wherein the DNA amplification reaction is a polymerase chain reaction (PCR).

3. The method of claim 1 wherein the enzyme of (b) is a DNA polymerase used in the DNA amplification reaction, or an RNAse.

4. The method of claim 1 wherein (c) comprises phosphoenolpyruvate synthase, phosphate and phosphoenolpyruvate.

5. The method of claim 1 wherein (c) comprises a combination of a nucleoside triphosphate-adenylate kinase, nucleoside 5'-triphosphate (NTP) and adenylate kinase.

6. The method of claim 1 wherein (c) comprises pyruvate phosphate dikinase.

7. The method of claim 1 wherein bioluminescent reagents comprise luciferin and luciferase.

8. The method of claim 7 wherein the bioluminescent reagents further comprise a source of magnesium ions.

9. The method of claim 1 wherein the bioluminescent reagents are added throughout the amplification reaction.

10. The method of claim 9 wherein the progress of the reaction is monitored throughout and this information is used in the quantification of the target DNA sequence in the sample.

11. A method of detecting a target DNA sequence in a sample, wherein the method comprises amplifying a target DNA sequence with a forward and reverse primer via polymerase chain reaction, wherein during amplification an RNA probe that comprises a complementary sequence to a region in the target DNA sequence being amplified is hybridized, and the hybridized RNA probe is hydrolyzed, producing adenosine monophosphate, converting the adenosine monophosphate to adenosine triphosphate with an enzyme, and detecting the presence of the target DNA sequence by a bioluminescence reaction.

12. The method of claim 11, wherein the bioluminescent reaction employs luciferin and luciferase.

* * * * *